United States Patent
Keskar et al.

(10) Patent No.: US 10,287,548 B2
(45) Date of Patent: May 14, 2019

(54) METHOD AND DEVICE FOR CLOSED SYSTEM CULTURE OF CARTILAGE TISSUE

(71) Applicant: General Electric Company, Schenectady, NY (US)

(72) Inventors: Vandana Keskar, Schenectady, NY (US); Weston Blaine Griffin, Niskayuna, NY (US); Xiaohua Zhang, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 155 days.

(21) Appl. No.: 15/197,508

(22) Filed: Jun. 29, 2016

(65) Prior Publication Data

US 2018/0002667 A1    Jan. 4, 2018

(51) Int. Cl.
| | | |
|---|---|---|
| *C12M 3/00* | (2006.01) | |
| *C12N 5/077* | (2010.01) | |
| *C12M 1/34* | (2006.01) | |
| *C12M 1/00* | (2006.01) | |
| *G01N 3/08* | (2006.01) | |
| *G01N 35/04* | (2006.01) | |

(52) U.S. Cl.
CPC ............ *C12N 5/0655* (2013.01); *C12M 21/08* (2013.01); *C12M 23/26* (2013.01); *C12M 41/40* (2013.01); *C12M 41/46* (2013.01); *G01N 3/08* (2013.01); *G01N 35/04* (2013.01); *G01N 2035/0465* (2013.01)

(58) Field of Classification Search
CPC ...... C12M 21/08; C12M 23/12; C12M 23/26; C12M 35/04; C12M 41/40; C12M 41/46; G01N 3/08; B30B 15/0094
See application file for complete search history.

(56) References Cited

U.S. PATENT DOCUMENTS

| | | | |
|---|---|---|---|
| 2,404,584 A * | 7/1946 | Liska ................. | G01N 3/18 374/52 |
| 6,037,141 A | 3/2000 | Banes | |
| 6,454,811 B1 | 9/2002 | Sherwood et al. | |
| 6,815,179 B2 | 11/2004 | Ochi et al. | |
| 7,198,908 B2 | 4/2007 | Ochi et al. | |
| 7,718,109 B2 | 5/2010 | Robb et al. | |

(Continued)

FOREIGN PATENT DOCUMENTS

DE    2932288 A *   6/1980   ............ G01N 3/08

OTHER PUBLICATIONS

English language machine translation of DE 2932288, pp. 1-4. Accessed Jun. 25, 2018 (Year: 2018).*

(Continued)

*Primary Examiner* — William H. Beisner
(74) *Attorney, Agent, or Firm* — Eversheds Sutherland (US) LLP

(57) ABSTRACT

The present approach relates to the design and use of a functionally closed bioreactor designed to immobilize, culture, and mature tissue on a loading platform. The bioreactor may be equipped with sensors for tissue monitoring which in conjunction with stiffness data can provide closed-loop control of tissue maturation. Based on a relationship between cartilage stiffness and tissue maturity, measurements of stiffness can be acquired and used as a surrogate for cartilage maturity without the need for destructive tests.

9 Claims, 11 Drawing Sheets

(56) References Cited

U.S. PATENT DOCUMENTS

| | | |
|---|---|---|
| 8,507,263 B2 | 8/2013 | Asnaghi et al. |
| 9,206,383 B2 | 12/2015 | Vunjak-Novakovic et al. |
| 2005/0153436 A1 | 7/2005 | Vilendrer |
| 2008/0026419 A1 | 1/2008 | Bottlang et al. |
| 2009/0298180 A1 | 12/2009 | Cattadoris et al. |
| 2015/0093777 A1 | 4/2015 | Marx et al. |

OTHER PUBLICATIONS

International Search Report and Written Opinion issued in connection with corresponding PCT Application No. PCT/EP2017/065916 dated Sep. 13, 2017.

* cited by examiner

METHOD AND DEVICE FOR CLOSED SYSTEM CULTURE OF CARTILAGE TISSUE

BACKGROUND

The subject matter disclosed herein relates to the field of tissue culture, and particularly to the field of cartilage tissue culture.

Engineered cartilage tissue may be grown in a research or medical context for use in various reconstructive procedures, including for use in reconstructive procedures related to the meniscus (present in certain joints) and intra-vertebral discs. Current fabrication processes for engineered cartilage tissue typically include a brief period of static culture followed by mechanical conditioning of the engineered tissue by uniaxial compressive loading. In practice, commercially available loading devices are for research scale applications and typically have drawbacks that include, but are not limited to: lack of real-time monitoring of the tissue structure and organization; lack of individual sample measurement data in real-time; destructive testing to acquire compression modulus measurement. Further, manual sample handling involved in the culture process (e.g., sampling the media, transferring the sample, adding media to the vessel, and so forth) introduces a high chance of contamination (i.e., ~10% failure rate).

As the technology matures and transitions from bench to commercialization, improved solutions for culturing engineered cartilage will be desirable.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a bioreactor system is provided. In such an implementation, the bioreactor system includes: a sample support table configured to hold one or more flexible vessels each containing one or more tissue samples; a force measurement sensor positioned so that when a respective flexible vessel is positioned on the sample support table at a measurement location, the respective flexible vessel rests on the force measurement sensor; an actuator configured to move along an axis to engage and disengage the respective flexible vessel when positioned at the measurement location such that, when engaged, the actuator generates a displacement and corresponding displacement data and the force measurement sensor measures the force and generates force data, wherein the data are used to generate a tissue stiffness measure.

In a further implementation, a method for culturing a tissue sample is provided. In accordance with this method, a tissue sample is immobilized on a tissue holder. The immobilized tissue sample and tissue holder are positioned within a flexible vessel. Culture medium is added to the flexible vessel and the flexible vessel is sealed. The flexible vessel is positioned on a table of a loading device. A linear actuator is operated to contact a first side of the flexible vessel so as to generate a changed force sensor reading on a second side of the flexible vessel opposite the first side.

In an additional implementation, a bioreactor system is provided. In such an implementation, the bioreactor system includes: a sample support table configured to hold one or more flexible vessels containing tissue samples; a first force measurement sensor positioned so that when a respective flexible vessel containing a tissue sample is positioned on the sample support table at a measurement location, the tissue sample is over the first force measurement sensor; a second force measurement sensor disposed about the first force measurement sensor in a plane of or parallel to the sample support table, wherein the first force measurement sensor and second force measurement sensor can move independent of one another in a first direction perpendicular to the plane of the support table when in use; and a linear actuator configured to move along an axis in the first direction and to come into contact with and displace the respective flexible vessel when the tissue sample of the respective flexible vessel is positioned over the first force measurement sensor.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 8 depicts an example of a screen of a tissue loading scheduler, in accordance with aspects of the present disclosure;

FIG. 9 depicts an example of a screen for configuring a measurement scheme, in accordance with aspects of the present disclosure;

DETAILED DESCRIPTION

Figure 1:
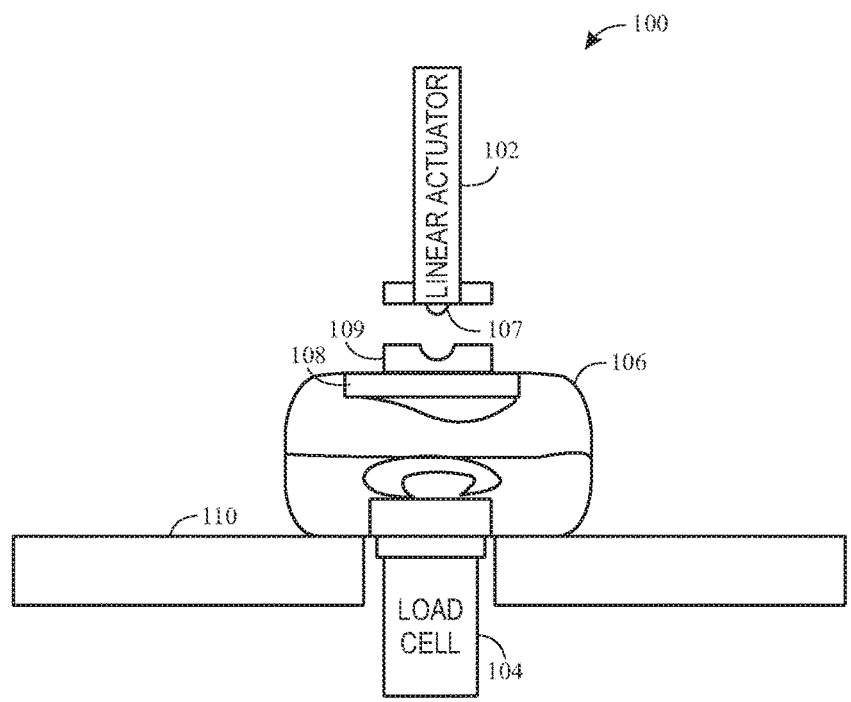
FIG. 1 depicts a front cut-away view of a loading device for use in tissue culture prior to engagement of a linear actuator, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As the technology associated with cartilage culture matures and transitions from bench to commercialization, alternate solutions for closed, automated tissue maturation with non-invasive evaluation of in-process cartilage constructs for better and faster tissue regeneration will be useful. The present approach provides various improvements to existing cartilage culture techniques by incorporating a closed or functionally closed bioreactor that is designed to immobilize, culture, and mature cartilage tissue on a loading platform (i.e., a platform configured to apply a force or load to a tissue sample) provided with stiffness measurement capability. As used herein, the term functionally closed should be understood to mean that the disposable kit employed may not be explicitly sealed, as shown in greater detail in certain examples provided herein. For example, vessels and/or tubing associated with the kit may have ports that can be used to transfer liquid material or gases. In the case of liquid material, the ports may support material additions/withdrawals with limited or minimum risk (e.g., a needleless-swabbable clave port or using a 0.2 um filter). In the case of inlet/outlet gases, a 0.2 um filter can be used. For the purposes of the present discussion, however, the presence of such ports or other access venues are consistent with a chamber, conduit, bag, or other kit that is understood to be functionally closed.

The bioreactor can also be configured to function inside a standard tissue culture incubator or alternatively, can be designed as a 'stand-alone' system for bench top culture. Thus tissue maturation can be fully automated to reduce labor and the chances of contamination due to open processes. Further, the bioreactor can be equipped with sensors for tissue monitoring which in conjunction with the stiffness data can provide for automated or semi-automated control of tissue maturation. In situ sensing of cartilage stiffness may be correlated to tissue maturity by taking samples for cell assays, biochemical tests, imaging, and so forth. Based on the relationship between cartilage stiffness and tissue maturity, measurements of stiffness can be acquired and used as a surrogate for cartilage maturity, thus eliminating the need for destructive tests. With this in mind, aspects of the present approach relate to the closed system culture of cartilage tissue in a uniaxial loading bioreactor equipped with in situ stiffness measurement capability.

By way of example, in accordance with certain implementations a functionally closed, uniaxial loading bioreactor system is provided that is designed for culture and maturation of cartilage tissue engineered for transplantation procedures, such as those related to joint or back reconstruction, repair, or treatment. The system itself is comprised of two components—a functionally closed flexible vessel (e.g., a container or bag having at least flexible side walls) that sits on a rotating table that is part of a uniaxial loading and measurement device (referred to herein as a "loading device" configured to apply a load or loading force along the direction of a single axis. In one implementation the functionally closed sterile vessel has media and gas exchange ports, as well as various sensors for facilitating the closed-loop control of the internal growing environment, such as pH sensors, oxygen sensors, temperature sensors, and so forth. The flexible vessel may also be designed to allow cartilage tissue immobilization during culture. Depending on the application the flexible vessel may be designed to provide the flexibility of holding one (or more) patient samples for autologous therapy or of holding multiple samples for allogeneic applications.

In one implementation, the loading device is capable of not only applying uniaxial compressive load to the cartilage tissue but is also capable of measuring tissue stiffness. In this manner, non-destructive monitoring of the tissue being cultured may be performed with the sample still in the functionally-closed flexible vessel. This is distinct from current cartilage bioreactors, which lack in situ stiffness measurement capability during mechanical loading of the tissue. In this manner, individual sample stiffness data may be obtained while the sample is being matured. A de-coupled linear actuator and force sensor configuration, wherein the force sensor is not collocated with the linear actuator displacement end, together with the engineered disposable flexible vessel, ensures the accurate stiffness measurement by minimizing the impact of the flexible vessel's deflection, as well as its film stiffness. The bioreactor system may be designed so as to be compact enough to fit inside a standard tissue culture incubator, but may also be configured to be a stand-alone bench top system regulating temperature and gas supply within the disposable flexible vessel.

As discussed in greater detail below, in certain implementations of the present approach a user immobilizes a tissue sample within the flexible vessel. In one implementations, the tissue sample(s) may be provided in the vessel by: (1) having the sample(s) 3D printed and placing the sample(s) into the individual tissue holder; or (2) directly 3D printing the tissues onto the individual tissue holders. As used herein, it should be understood that 3D printing encompasses any additive manufacturing or deposition approach suitable for sample generation (such as generation of a multi-layer or three-dimensional sample) in an additive manner. In other implementations the tissue sample may be provided in the vessel by other means, including, but not limited to, compression molding de-cellularized matrix or other suitable approaches.

The flexible vessel is then sealed, filled with required amount of culture medium through ports and positioned onto the rotating table. In one implementation, the tissue sample(s) may be moved or rotated between a set of radial positions, one of which constitutes a measurement position where linear force and force measurements are acquired (i.e., a position in which the sample is loaded for measurement). In one such example, the tissue sample(s) may be sequentially moved or rotated between positions, as discussed in greater detail below, by raising the associated support table using a solenoid to a positioning height and rotating the table to the next sequential sample position, at which point the table can be lowered to a measurement height. That is, when lowered the tissue sample rests on a force sensor (e.g., a load cell) situated below the table, while allowing the tissue bag to rest on the table. As will be appreciated, other position and movement schemes may alternatively be employed. In particular, those skilled in the art will appreciate that there are multiple approaches, in addition to those discussed herein, for achieving the degrees of freedom necessary to position the sample on the force sensor and in the line of action between a linear actuator and the force sensor.

In one implementation the linear actuator then moves downward. Depending on the embodiment, the linear actuator may be a piezo-walker or stacked-type linear motor, a voice coil type linear motor, a hydraulic actuator, a lead screw drive system, a rack-and-pinion, and so forth. Prior to the linear actuator contacting the tissue, the force sensor (e.g., load cell) reading remains the same. Thus, a change of the force sensor reading indicates the onset of loading the tissue using the linear actuator. This position is recorded as the initial loading position. The linear actuator then loads the tissue cyclically according to the user input (e.g., loading time, frequency, amplitude, and offset). The displacement and force during the loading may be logged and used for calculating the real-time stiffness. The sample is loaded for any specified period of time (user or computer input) before moving to the next sample. The process then repeats itself.

With the preceding summary in mind, the following sections provide additional, detailed discussion of certain relevant aspects of the present approach.

Figure 2:
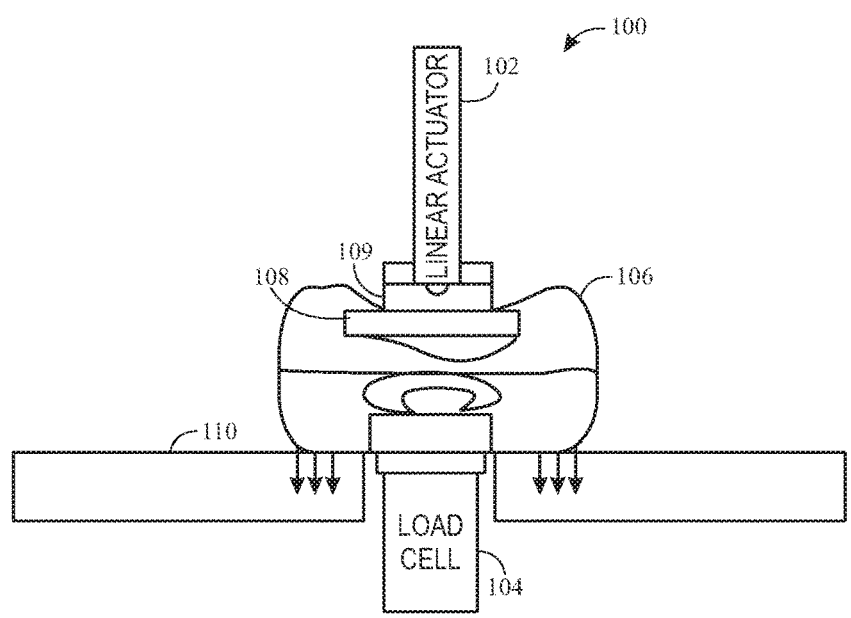
FIG. 2 depicts a front cut-away view of the loading device of claim 1 after engagement by the linear actuator, in accordance with aspects of the present disclosure.

LOADING DEVICE—With respect to the loading device, in one implementation a loading device 100 has a linear actuator 102 and a force sensor 104 that are decoupled from one another and that are positioned on opposed sides, as shown in FIGS. 1 and 2 in the context of a flexible vessel 106 prior to loading (FIG. 1) and after loading (FIG. 2). In the depicted example of FIGS. 1 and 2, the linear actuator 102 engages with the top loader cap 109 of the disposable flexible vessel 106 and then compresses the flexible vessel 106 to apply a load the tissue sample. Though not shown in FIGS. 1 and 2 (or FIGS. 3 and 4 discussed below), a controller (either processor-based and/or in the form of one or more application specific integrated circuits) may be provided in communication with one or both of the linear actuator 102, force sensor 104, and/or table 110 to operate these components as discussed herein, as well as to process data generated by the linear actuator 102 and force sensor 104 to calculate measurements and/or derived values as discussed herein.

In one implementation, the disposable flexible vessel 106, which houses the tissue and culture medium, is constructed with flexible ethylene-vinyl acetate (EVA)/polyethylene film material. Other suitable vessel materials include, but are not limited to EVA only as well as other flexible biocompatible film materials. Further, though the present examples describe vessels 106 formed using film-based materials, in other implementations the flexible vessel 106 may be formed instead using blow-molding processes, a thermoforming process, or a compression molding process. The structure of the flexible vessel 106 allows for deformation when it is under compression from the linear actuator 102, as shown in FIG. 2. The deformation of the top surface of the flexible vessel 106 transfers its reacting force to its four sides, which is further transferred onto the table 110, as shown by the downward arrows in FIG. 2. In this way, the stiffness of the flexible vessel 106 does not affect the force sensor reading. The force sensor 104 would only respond to the event when the top loader 108 comes in contact with the tissue sample 132 and thereby the tissue deforms under the compression. As a result, the force sensor reading would be the true loading force on the tissue.

Figure 3:
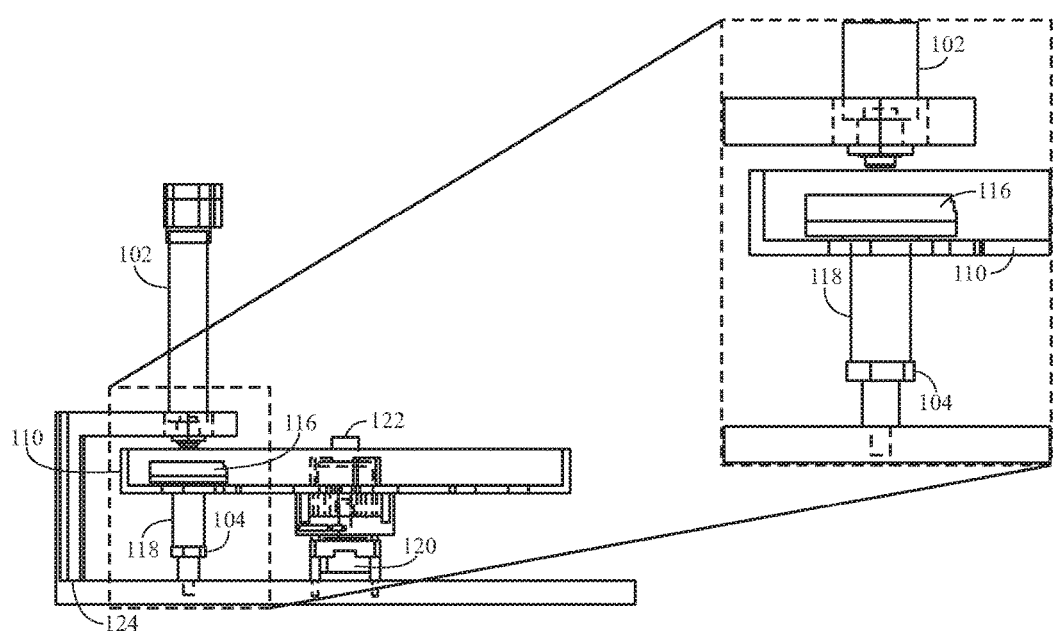
FIG. 3 depicts a view of a loading device for use in tissue culture with an inset blow-up view of a decoupled linear actuator and force sensor of the device, in accordance with aspects of the present disclosure.

An implementation of the loading device 100 having a de-coupled linear actuator 102 and force sensor 104 (e.g., load cell) configuration is shown in FIG. 3, including an inset showing an enlarged depiction of the linear actuator 102, force sensor 104, and a tissue holder 116 configured to hold a tissue sample within a flexible vessel 106 (not shown). In the depicted example of FIG. 3, the force sensor 104 (e.g., a load cell) is associated with a force sensor rigid extension rod 118 configured to transmit the force applied to the tissue holder 116 to the force sensor. In addition, FIG. 3 depicts a rotational motor 120 (e.g., a stepper motor) and solenoid 122 assembly used to lift, rotate, and lower the table 110 during operation, as discussed herein.

In one implementation the linear actuator 102 has a resolution in the range of 0.1 um-5 um, such as a 0.2 µm resolution. The force sensor 104 may have a sensitivity in the range of 18.0-200 mV/N, such as a 90.9 mV/N sensitivity. By way of example, a linear actuator 102 having a 0.2 µm resolution used in conjunction with a force sensor 104 having a 90.9 mV/N sensitivity can accurately measure tissue stiffness in a range from 10 kPa to 200 kPa, which cover the range of different tissue types in their maturing processes in typical applications. As discussed herein, the loading device 100 is capable of using real-time stiffness data to vary loading patterns in order to meet the set target stiffness, e.g. loading and unloading time, frequency, amplitude, and offset.

DISPOSABLE FLEXIBLE VESSEL DESIGN WITH TISSUE HOLDER ASSEMBLY FOR CARTILAGE TISSUE—While the preceding relates to the loading device 100, the flexible vessel 106 is now discussed in greater detail. As discussed herein, in certain implementations the individual tissue holder can house one or more tissue samples. In accordance with certain configurations, each sample may have a tissue holder 116 which rests on a universal plate holder 130, which in turn is positioned on a universal plate holder cap 131, as shown in exploded view in FIGS. 4 and 5.

The flexible vessel 106 (shown in the process flow of FIG. 6) is sealed on three sides, with one side left open for tissue holder 116 insertion. In practice, both disposable flexible vessel 106 and its corresponding tissue holder 116 are gamma sterilized in advance. In such a sterile implementation, the user will typically open the gamma sterilized flexible vessel and tissue holder in a biosafety cabinet. The user then places the cartilage tissue 132 on the tissue holder 116 and fixes its horns by a tissue clamp 134. All components of the flexible vessel 106 and/or tissue holder 116 that are in direct contact with cells will typically be fabricated using bio-compatible material. Once the tissue 132 is fixed on the tissue holder 116, the user inserts the tissue holder 116 into the disposable flexible vessel 106, the steps of which are shown in the process flow of FIG. 6.

Figure 4:
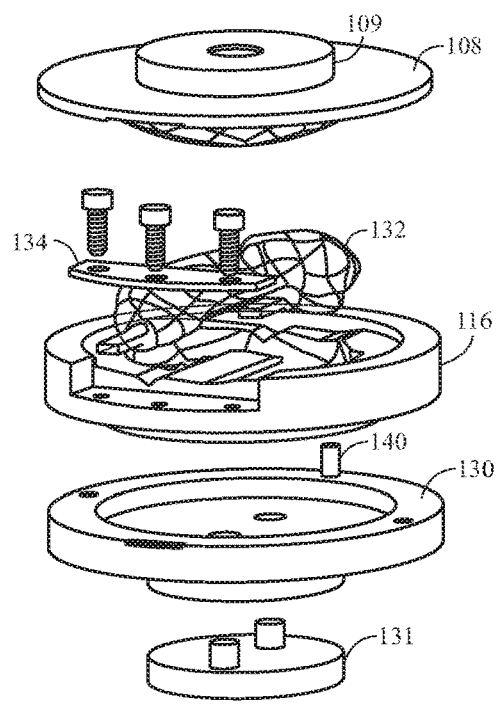
FIG. 4 depicts an exploded view of a tissue holder assembly, in accordance with aspects of the present disclosure.
Figure 5:
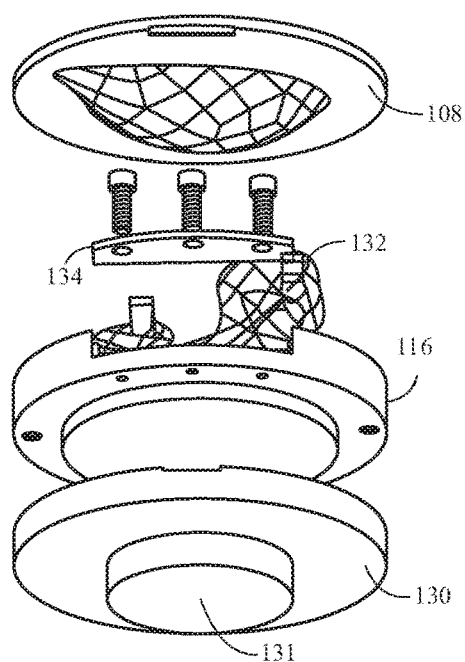
FIG. 5 depicts an alternative exploded view of a tissue holder assembly, in accordance with aspects of the present disclosure.

In one implementation, as illustrated in FIG. 4 and FIG. 5, a stainless steel (e.g., stainless steel 316) dowel pin 140 of the universal plate holder 130 aligns with a corresponding hole in the tissue holder 116. Magnets embedded in the tissue holder 116 may be employed to attach to steel pins on the universal plate holder 130 to immobilize the tissue holder 116 with respect the plate holder 130. In one embodiment, both embedded magnets and steel pins are covered with epoxy (e.g., Loctite M-21HP epoxy) to prevent culture exposure to the steel pins and magnets.

In one implementation, the bottom film material has corresponding holes to allow universal plate holder cap 131 to feed through the bottom film material. The universal plate holder cap 131 fits into the holes on the universal plate holder 130. Epoxy (e.g., M-21 HP epoxy) may be applied to bind universal plate holder 130, film, and universal plate holder cap 131. The epoxy, when present, also provides a proper seal between the film and universal plate holder cap 131. The top loader cap 109, top film, and top loader 108 may be bound together using the same or a comparable approach.

Figure 6:
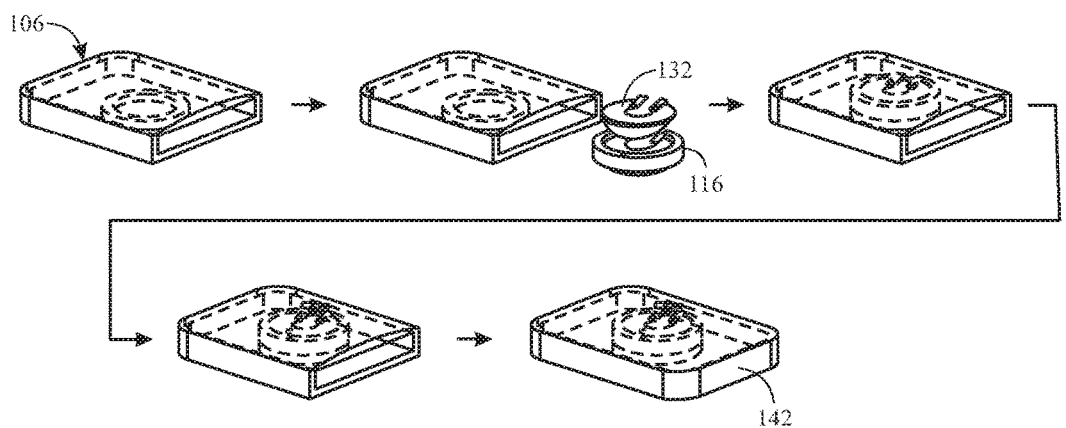
FIG. 6 depicts a process flow of a tissue placement process, in accordance with aspects of the present disclosure.

After the tissue assembly is placed inside the disposable flexible vessel 106, the user seals the open side of the flexible vessel 106 with a bar (heat) sealer, creating a sealed end 142 as shown in the last step of FIG. 6. In certain implementations each disposable flexible vessel 106 has at least one gas exchange port and one medium exchange port. The tissue 132 is submerged in the medium (regardless of loading or not) to allow cell growth.

As discussed herein, the disposable flexible vessel 106 has one or more magnets attached to the bottom surface of the flexible vessel 106. These magnets help hold the flexible vessel onto the table 110. The flexible vessel's bottom plate aligns with a hole in the table 110. This ensures the tissue 132 is in the right location relative to the linear actuator 102 and force sensor 104. The table 110 will rotate so that multiple tissues can be loaded in a sequence with a fixed axial position of the linear actuator 102 and force sensor 104.

As shown in FIG. 3, in one implementation the table 110 is lifted by a solenoid actuator 122 that controls the up and down motion of the table 110. The table 110 is rotated by a rotational motor (e.g., stepper motor) 120 that rotates the table 110 (and disposable flexible vessel 106 in which the tissue sits) between rotational positions, such as to a loading position. When in the loading position, as shown the table 110 is lowered, which allows the bottom plate of the disposable flexible vessel rest on the force sensor 104 through force sensor extension rod 118. During the loading period (for tissue maturation), the linear actuator 102 comes down and engages with the tissue top loader cap 109, which is bonded with top loader 108. The linear actuator 102 continues to move the tissue top loader 108 until it comes in contact with the tissue 132 and applies cyclic load. The top loader 108 is separated from the tissue 132 during the unloaded periods.

By way of example, one implementation of a particular embodiment is described in greater detail. In this example, there are at least two air dampers used to smooth out the otherwise high solenoid 122 acceleration and deceleration. This ensures the table 110 is lifted or lowered in a gentle manner, thus minimizing the mechanical shock to the flexible vessel 106 and tissue 132 inside. Prior to lowering the table 110 into position, a hall sensor may be used to verify that the table 110 is at the correct rotational position relative to the force sensor and linear actuator line of action. By way of example, in one implementation there are equal numbers of magnets embedded underneath the table 110 as the number of positions where the tissues 132 are located. When a given magnet is positioned next to the hall sensor, which may be fixed in the stationary table base 124, it can determine if the table 110 has moved to the correct location or has been prevented from reaching the correct location. In the event that the table 110 is prevented from reaching the correct position, the following events would occur sequentially: (1) the hall sensor output would not be in the expected state, (2) the program would be stopped, and (3) the program would output an error message to notify the user. Slip ring connectors may be used to make electrical connection between the rotating solenoid 122 (fixed to the table 110) and the stationary table base 124.

While the preceding Hall sensor implementation is one example of an approach for rotating the table 110 during operation, other approaches are also possible. For example, instead of using a Hall sensor at each location, a rotational motor 120 with an absolute encoder coupled to the rotary stage (i.e., table 110) may instead be employed. In this way, even if the motion is blocked or the table 110 was prevented from reaching the final location, the controller would be aware.

In one implementation, the solenoid driver implements a peak-and-hold driver current strategy to lower its power consumption and thus to avoid excessive heat generation when solenoid actuator 122 is energized. With respect to the linear actuator 102, this actuator may couple with the top loader cap 109 of the flexible vessel 106 using a self-aligning feature, such as a hemi-sphere 107 and matched depression in top loader cap 109, which allows small misalignment between the actuator 102 and the flexible vessel 106.

The starting position of the tissue loader 100 may be determined by multiple methods, two examples of which are discussed herein though other approaches may be equally suitable. By way of example, one method is referred to as the 'touch point' method herein. The steps associated with the 'touch point' method are as follows. First the user specifies a threshold voltage of the force sensor 104 output. The linear actuator 102 drives the top loader 108 at a constant low speed. With an appropriately selected threshold voltage, the flexible vessel 106 deforms as the loader engages the flexible vessel but the deformation would not cause the force sensor reading to exceed the threshold as long as the top loader is not touching the tissue. As soon as the top loader 108 comes in contact with the tissue 132, the force sensor 104 voltage begins increasing. When the force sensor 104 output (or change in output) reaches a user specified threshold value, the linear actuator 102 stops and this position is stored as the start loading position of this particular tissue sample. The 'touch point' method may be subject to certain errors due to the delay between when the force sensor 104 reading exceeding threshold and when the linear actuator 102 position is registered.

Figure 7:
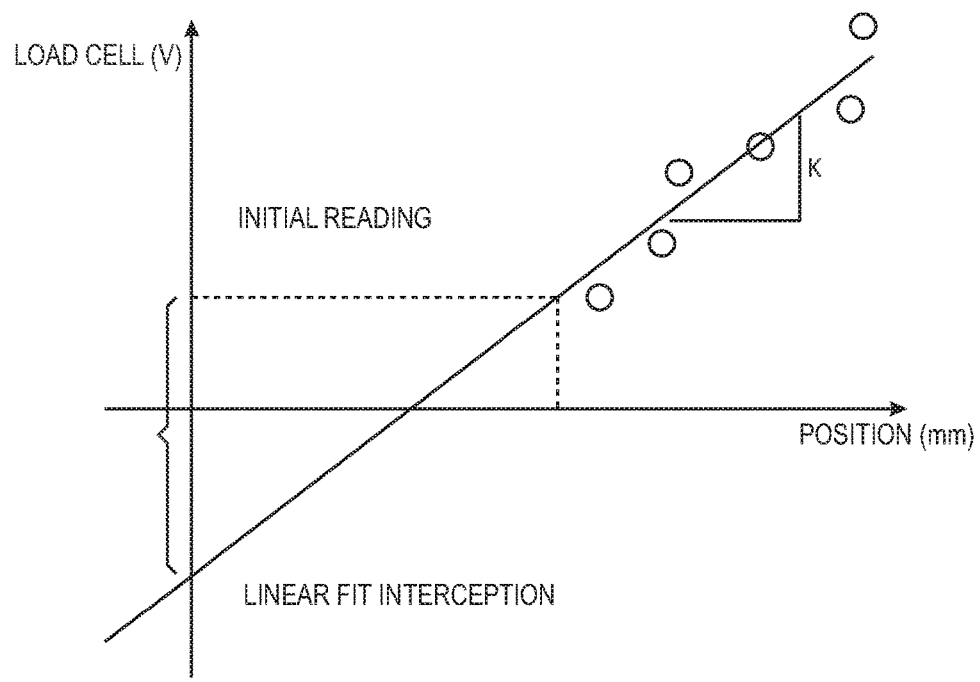
FIG. 7 depicts a graph showing the determination of initial loading position using linear regressive methods, in accordance with aspects of the present disclosure.

A second method described herein is called the 'regressive' method. In this method, the top loader driven 108 by the linear actuator 102 is driven to the tissue 132 as described in the 'touch point' method. Next, the linear actuator 102 continues to compress the tissue sample 132 even though the force sensor 104 output has exceeded a user specified threshold value. The positions of the linear actuator 102 and the force sensor 104 outputs for each tissue sample over a small displacement are stored and, when the force sensor 104 output reaches a specified upper limit (which can be set greater than the threshold), the linear actuator 102 stops. The slope and they intersect of the linear fit are calculated using the linear actuator positions (x) and their corresponding force sensor outputs (y), as shown in the linear regression example of FIG. 7. Assuming the tissue has a constant stiffness at the beginning of the loading, with this slope and y intersect, the zero loading position of the tissue sample 132 is computed and this position is stored as the start loading position of this particular tissue sample. Compared to the 'touch point' approach, the 'regressive' method may have reduced error due to taking multiple force sensor readings and their corresponding linear actuator positions and assuming a linear stiffness during the initial tissue deflection. The likelihood of the random error due to the time delay can thus be lowered.

Figure 8:
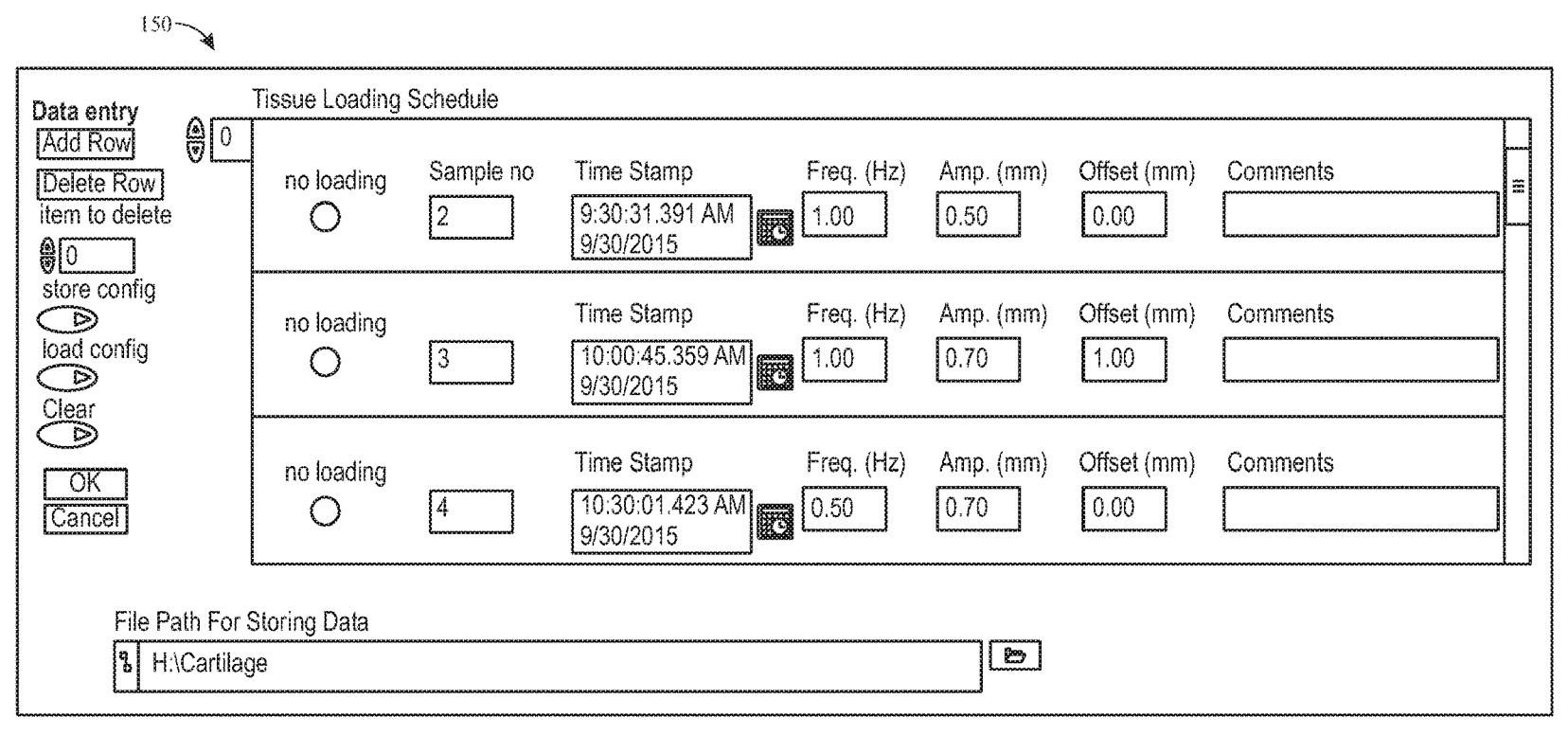

TISSUE LOADING SCHEDULER—While the preceding describes various mechanical, structural, and operation aspects of the present approach, a further aspect to be described is the scheduling component. In one implementation, the user schedules a loading sequence and pattern using a tissue loading scheduler provided in the form of a computer stored and executed loading application. Examples of sample screens for one such application are provided in FIGS. 8 and 9. In this example, a first window 150 (shown in FIG. 8) is displayed initially and prompts user input when the program is run. Via these screens and windows, the user can schedule any particular sample to be loaded at a certain time. In the depicted example, the times are scheduled sequentially. In other words, the earlier times would be scheduled in front of later times. Under control of the scheduling application, the table 110 would move the corresponding tissue sample 132 to the axis where linear actuator 102 and force sensor 104 are located (i.e., the loading position) when the specified time is reached. Then, if the loading is scheduled, the program will utilize user inputs (frequency, amplitude and offset), if provided, and command the linear actuator 102 to load the tissue 132 with corresponding sinusoidal function. The loading stops and the linear actuator 102 retracts. When the time reaches the next scheduled time, the table 110 then moves the next sample to the loading position and the process repeats.

Figure 9:
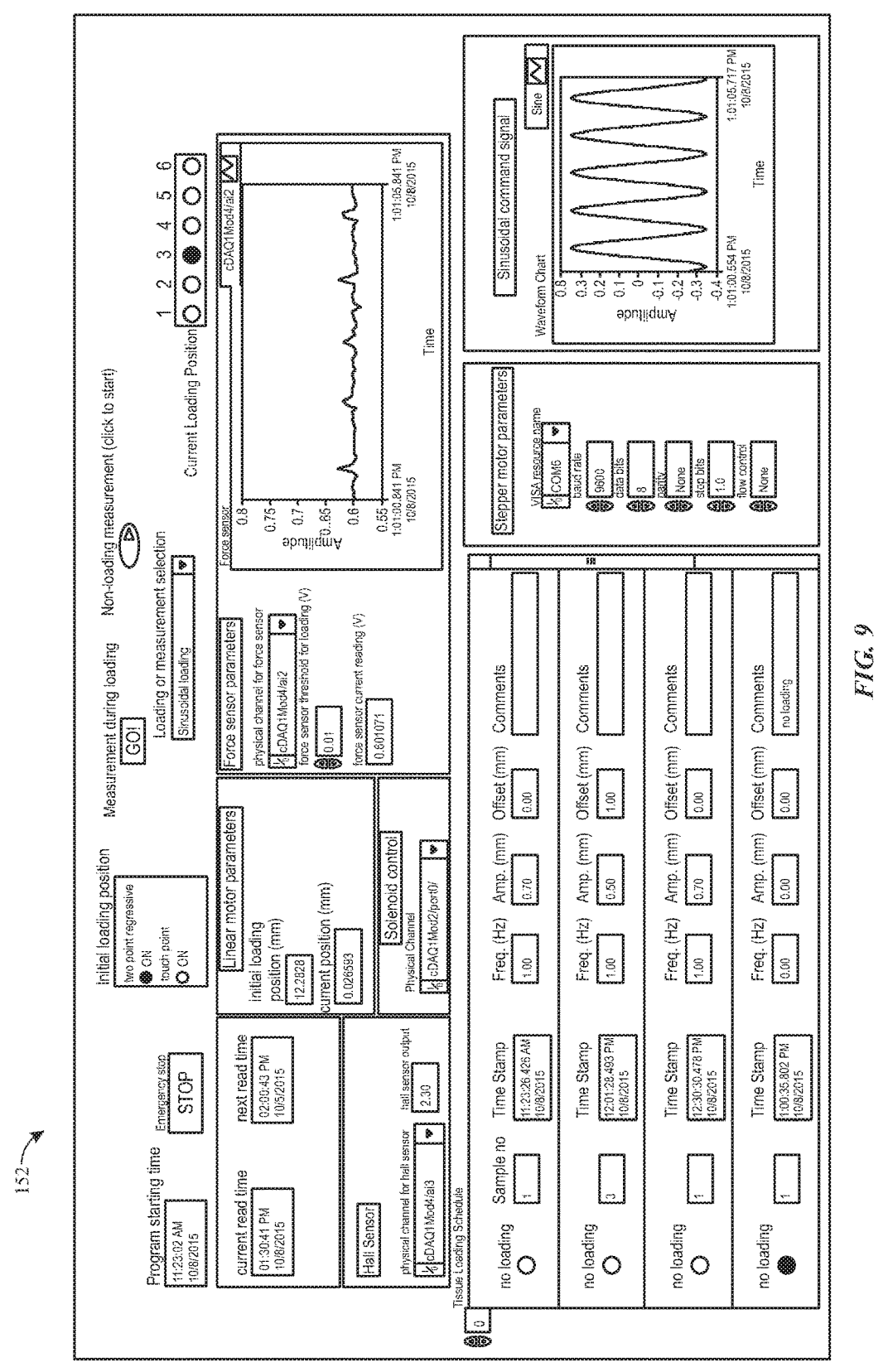

FIG. 9 shows an additional example of a display 152 (e.g., a front panel display of a programmed or dedicated device) of the main program. In one implementation, as the program is running, the user can interrupt the program and perform a measurement. In one embodiment, the user can direct the system to obtain a computed value for tissue stiffness derived from the periodic loading (e.g., sinusoidal loading) of the tissues. Additional or alternative schemes may also be used to acquire a specified number of measurements using other loading schemes, and the program will automatically store at least a portion of the data for the linear actuator 102 position and force sensor 104 output during a loading period in a scheduled sequence. Examples of other measurement schemes include stress relaxation and frequency sweep. For example, in a stress relaxation measurement context, the user may be allowed to specify a given number of steps (e.g., three steps), their respective positions, and holding times for each stress relaxation measurement. In one example, the position and force data will automatically be recorded during the entire measurement. Similarly, the user may be allowed to specify some maximum number (e.g., three) of frequencies, their respective amplitudes, sweeping times, and offset for each frequency sweep measurement. Again, the position and force data may be automatically saved during the entire measurement.

NON-DESTRUCTIVE CARTILAGE TISSUE MODULUS MEASUREMENT—With the preceding in mind, further aspects related to non-destructive tissue modulus measurement are described.

Figure 10:
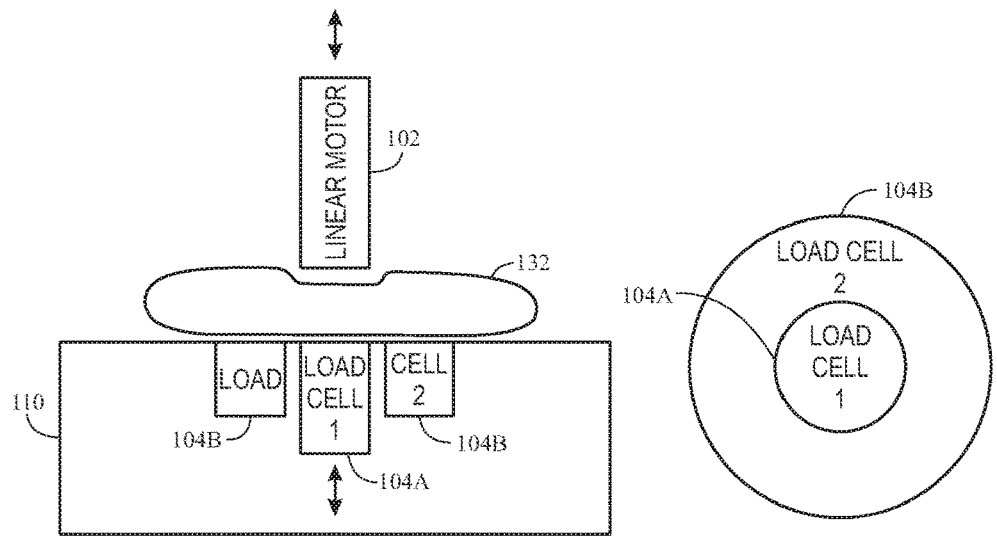
FIG. 10 depicts a cut-away side and top-down view of a pair of concentric force sensors for measuring modulus, in accordance with aspects of the present disclosure.

The traditional method of determining the material's modulus involves cutting a known geometry sample and testing the stress-strain characteristic of the known geometry sample. This is typically destructive due to the fact that a specific sample size is required and thus it usually needs to be isolated from the rest of the sample. In accordance with the present approach, a sample's local Young's modulus and Poisson's ratio are instead measured without preparing the specific sample dimension, thereby avoiding physical isolation of a tested sample from the larger of the sample. In accordance with this approach, Young's modulus and Poisson's ratio are determined by using both contact modulus measurement and shear modulus measurement. In one implementation, the two measurements can be acquired using force sensors 104A, 104B provided as concentric cylinders, as shown in FIG. 10. In particular, in the depicted example a first force sensor 104A is provided as a cylindrical cell 104 nested within a second cylindrical force sensor 104B that is annular in configuration, i.e., a cylindrical ring.

Referring to FIG. 10, to measure contact modulus, the top surface (i.e., the measurement surface) of first force sensor 104A remains in flush with top surface of the second force sensor 104B. The linear actuator 102 deforms the sample 132 and the first force sensor 104A measures the compressive force.

To measure shear modulus, the cylindrical first force sensor 104A is moved downward, relative to the surface of the table 110 and the second force sensor 104B. In this manner a recess is formed relative to the measurement surface of the second force sensor 104B, which can thereby be used to measure the shear force. The Young's modulus and Poisson's ratio can be derived using these two force measurements. In one implementation, the measurements can be performed without direct contact with the sample 132, e.g., through a film material.

Figure 11:
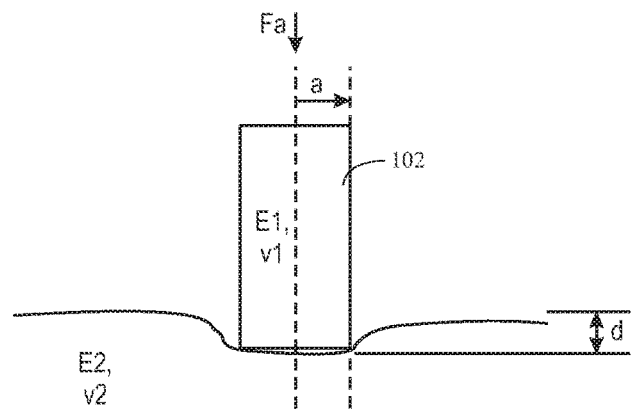
FIG. 11 depicts parameters for a contact modulus measurement, in accordance with aspects of the present disclosure.

With respect to these values and their calculation, contact modulus can be defined by the following parameters, with reference to FIG. 11 for a graphical illustration of the described context. In this context, d is the vertical displacement or distance associated with the recess and a is the radius of the first force sensor 104A, and v is Poisson's ratio. By definition axial force $F_a$:

$$F_a = 2aE^* d \quad (1)$$

where, $E^*$ is the contact modulus:

$$\frac{1}{E^*} = \frac{1-v_1^2}{E_1} + \frac{1-v_2^2}{E_2}. \quad (2)$$

For steel (here representing the linear actuator contact 102), $E_1$=200 GPa, $v_1$=0.3, while for a tissue sample 132, $E_2$=10~200 kPa, $v_2 \approx 0.4$. The term $$\frac{1-v_1^2}{E_1}$$

is several orders of magnitude lower than the term $$\frac{1-v_2^2}{E_2}.$$

Therefore, equation (2) can be approximated as $$\frac{1}{E^*} = \frac{1-v_2^2}{E_2}.$$

Substituting $$\frac{1}{E^*} = \frac{1-v_2^2}{E_2}$$

into (1) gives:

$$\frac{F_a}{d} = \frac{E_2 \cdot 2a}{1-v_2^2}. \qquad (3)$$

Writing $E_2$ as E and $v_2$ as v, gives:

$$\frac{F_a}{d} = \frac{E \cdot 2a}{1-v^2}. \qquad (4)$$

Figure 12:
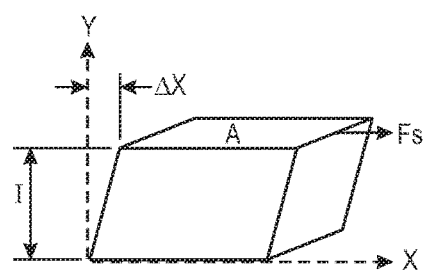
FIG. 12 depicts aspects of a shear modulus definition, in accordance with aspects of the present disclosure.

For shear modulus, by definition, and with reference to FIG. 12:

$$G = \frac{F_S \cdot l}{A \cdot \Delta x} \qquad (5)$$

where G is the shear modulus, $F_s$ is the shear force, and the remaining parameters correspond to the measures and concepts illustrated in FIG. 12, such as, A corresponding to a surface area of the sample 132, $F_s$ corresponding to a shear force, $\Delta x$ corresponding to a deformation, and l corresponding to a sample height.

Figure 13:
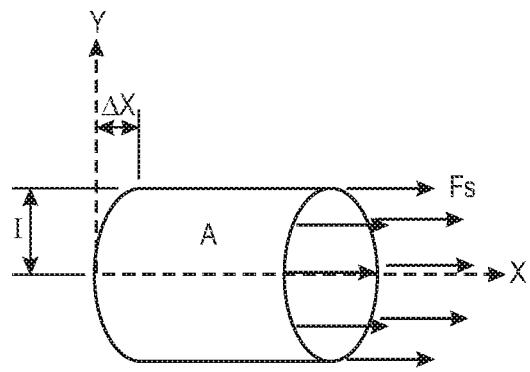
FIG. 13 depicts aspects of a transformed shear modulus definition, in accordance with aspects of the present disclosure.
Figure 14:
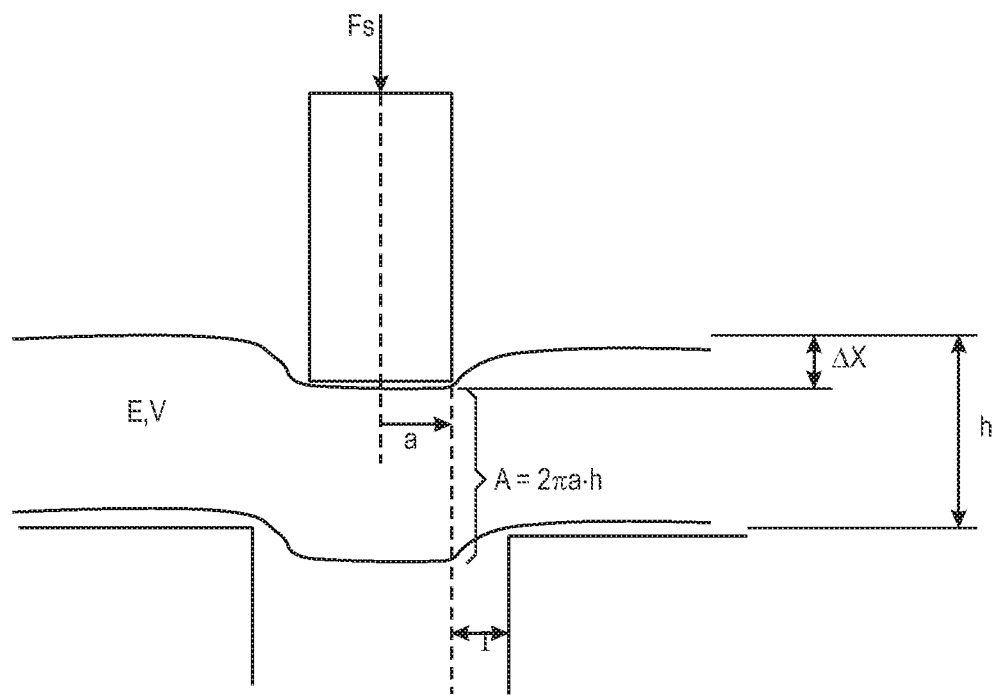
FIG. 14 depicts parameters for a shear modulus measurement, in accordance with aspects of the present disclosure.

With this in mind, consider revolving the standard shear configuration 360° around an x-axis, as shown in FIG. 13. In this example, FIG. 13 illustrates the transformed shear modulus, which assumes fixed length on the x-axis (or zero deformation on the x-axis). If the fixed axis becomes a fixed cylinder with radius of a, then the shear modulus definition can be configured as shown in FIG. 14. Shear modulus G can then be determined by this configuration.

By definition:

$$E = 2G(1+v) \qquad (6)$$

By substituting equation (5) into (6) and providing $A = 2\pi a \cdot h$:

$$E = 2\frac{F_S \cdot l}{2\pi a \cdot h \cdot \Delta x}(1+v). \qquad (7)$$

Solving equations (4) and (7) for Poisson's ratio, v, gives:

$$v = 1 - \frac{2F_s \cdot l \cdot d}{F_a \cdot \pi \cdot h \cdot \Delta x}. \qquad (8)$$

Substituting equation (8) into (7) gives:

$$E = \frac{F_S \cdot l}{\pi a \cdot h \cdot \Delta x}\left(2 - \frac{2F_s \cdot l \cdot d}{F_a \cdot \pi \cdot h \cdot \Delta x}\right). \qquad (9)$$

With the preceding in mind, if the configuration is known (i.e., if l, d, and h are known), by measuring axial force $F_a$, shear force $F_s$, and deformation $\Delta x$, one can calculate Poisson's ratio v and Young's modulus E from equations (8) and (9). With this in mind, and as noted above, axial force $F_a$ and shear force $F_s$ can be read from the first cylindrical force sensor 104A and second cylindrical force sensor 104B, respectively.

Figure 15:
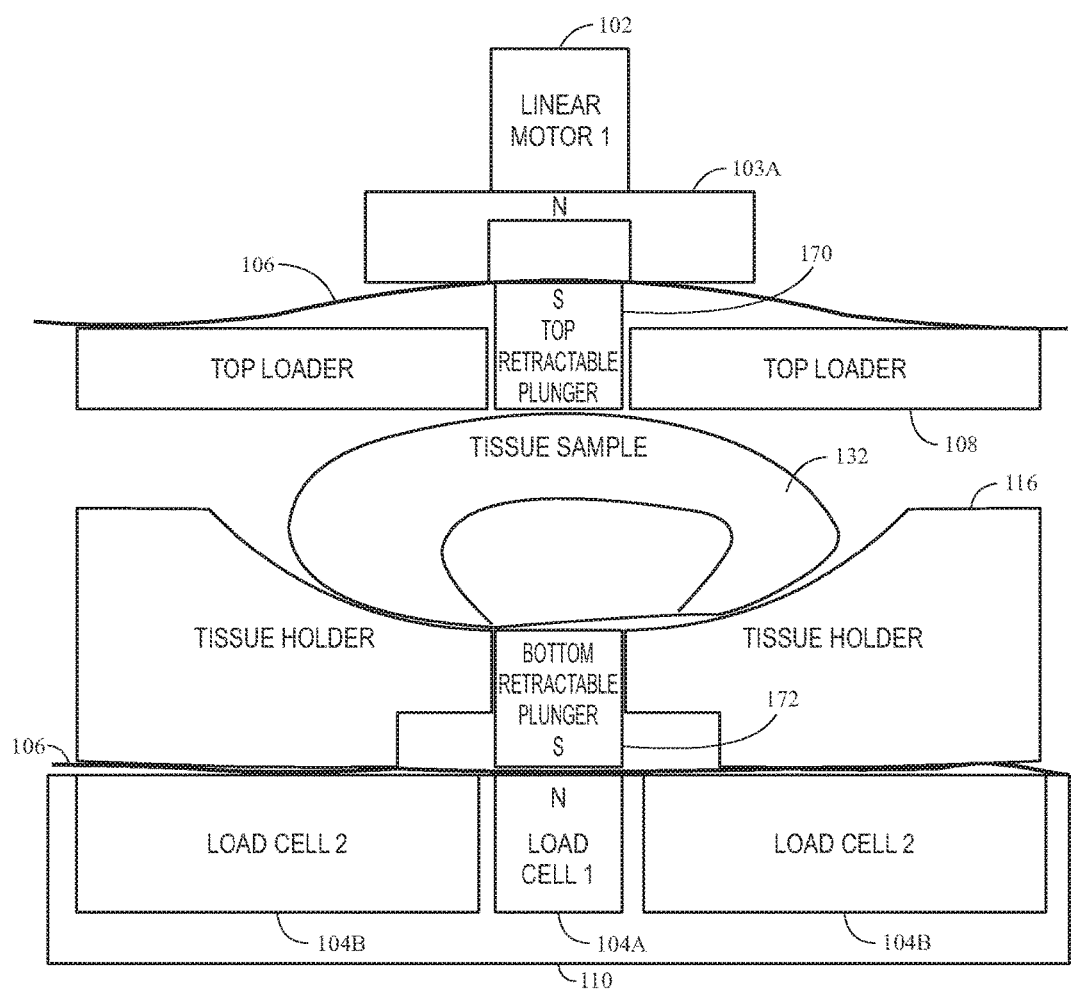
FIG. 15 depicts normal loading of a tissue sample inside a flexible vessel, in accordance with aspects of the present disclosure.

Further, in accordance with certain implementations, the modulus may be measured through a film material (i.e., flexible vessel 106) without direct contact with the sample 132. For example, FIG. 15 shows a configuration of a normal loading of a tissue sample 132 inside a disposable flexible vessel 106. As in preceding examples, the tissue sample 132 sits on a tissue holder 116. In the depicted example, the top loader 108, together with top plunger 170, both engaged by the coupler 103A, come down and load the tissue 132 without affecting the force measurement underneath the tissue holder 116. The combined reading of the first force sensor 104A and the second force sensor 104B is the total loading force, which can be used to determine tissue stiffness as described above. In certain embodiments, the components inside the disposable flexible vessel 106 are made of bio-compatible material. As may be appreciated from the depicted example, in such an implementation the film (i.e., flexible vessel 106) is located outside the tissue holder 116 and top loader 108 while still able to provide sealing.

To measure the tissue modulus, both axial force ($F_a$) and shear force ($F_s$) need to be measured in the compression and shear configuration, as discussed above. The measurement of the axial and shear forces in known configurations allows one to generate the two equations (8) and (9) and solve for the two unknowns, the tissue modulus and Poisson's ratio. Further, the loading and measurement portion should be movable in order to apply the axial and shear forces over a known area or length, respectively. To accomplish this, in one implementation a portion (i.e., the top retractable plunger 170) of the top loader 108 is detached from the remainder of the top loader 108. Likewise, in one such implementation, a portion (i.e., the bottom retractable plunger 172) of tissue holder 116 is detached from the remainder of the tissue holder 116. In one such implementation, the top retractable plunger 170 engages with the coupler 103B of linear actuator 102 and can move the plunger 170 separately from the top loader 108. In this way, with a coupler change, it is possible to apply the axial force ($F_a$) and shear force ($F_s$) as discussed above or apply the normal loading of the tissue for maturation. The engagement of top retractable plunger 170 to the coupler 103B can be controlled by magnets (as indicated by the north (N) and south (S) pole indications in the figures). The attractive force between the magnets in the coupler 103B and the top retractable plunger 170, ensure that the top retractable plunger 170 moves together with motion generated by the linear actuator 102. The flexibility in the top film 106 allows the relative motion between the top loader 108 and the top retractable plunger 170.

Figure 16:
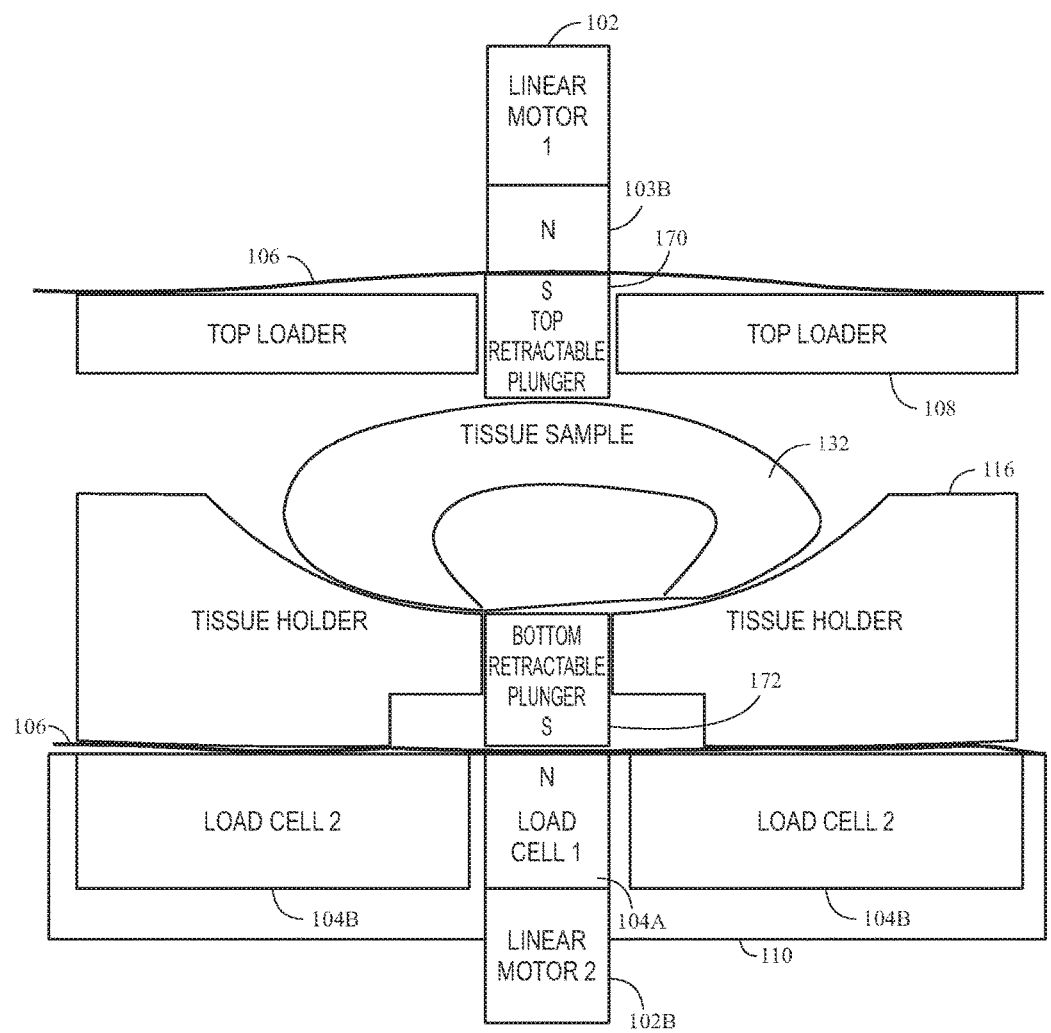
FIG. 16 depicts a contact modulus measurement configuration, in accordance with aspects of the present disclosure.

To obtain the compressive force measurement as shown in FIG. 16, a first linear actuator 102 engages with a different tool (coupler 103B) than in the normal loading (coupler 103A), which allows the first linear actuator 102 to push only on the top retractable plunger 170. The change of the first force sensor 104A and second force sensor 104B readings in such a configuration can be equated to the axial force $F_a$. Thus, the area of the top plunger 170 and the displacement of the linear 102, with the axial force $F_a$, are then used to partially complete equation (8) with tissue modulus and Poisson's ratio still unknown.

Figure 17:
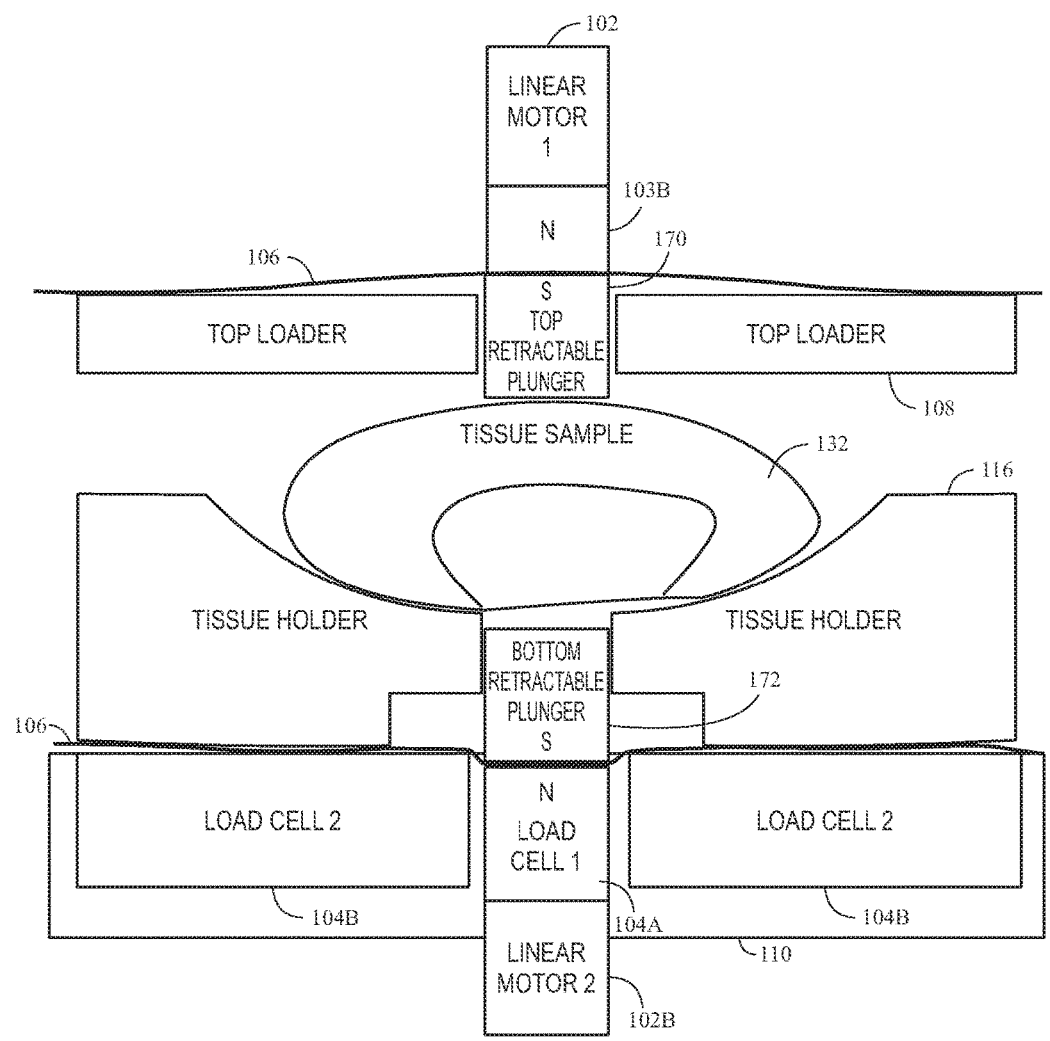
FIG. 17 depicts a shear modulus measurement configuration, in accordance with aspects of the present disclosure.

As shown in FIG. 17, for shear measurement, the bottom retractable plunger 172 is pulled downward by retraction of the first force sensor 104A, which is coupled with a second linear actuator 102B. This arrangement allows the second force sensor 104B to measure the shear force $F_s$. Again, the shear line length (i.e., the perimeter of the opening in tissue holder 116 where the bottom retractable plunger 172 fits), the displacement of the first linear actuator 102, and the shear force $F_s$ are then used to partially complete equation (9) with tissue modulus and Poisson's ratio still unknown.

After both force measurements are obtained, along with other geometric dimensions, equation (8) and (9) can be used to calculate the Poisson's ratio and Young's modulus as discussed above. Though not shown in FIGS. 15-17, a controller (either processor-based and/or in the form of one or more application specific integrated circuits) may be provided in communication with one or both of the linear actuator(s) 102, force sensor(s) 104, and/or table 110 to operate these components as discussed herein, as well as to process data generated by the force sensor(s) 104 to calculate measurements and/or derived values as discussed herein. It should be noted that, many experiments can be done in similar manners as described herein to obtain different sets of measurement data. Averaging algorithms can be applied to reduce single measurement error and obtain statistically significant values.

Technical effects of the invention include a functionally closed bioreactor that is designed to immobilize, culture, and mature cartilage tissue on a loading platform (i.e., a platform configured to apply a force or load to a tissue sample) provided with real-time stiffness measurement capability. The bioreactor can be configured to function inside a standard tissue culture incubator or alternatively, can be designed as a 'stand-alone' system for bench top culture. Tissue maturation can be fully automated to reduce labor and chances of contamination due to open processes. Further, the bioreactor can be equipped with sensors for tissue monitoring which in conjunction with the real-time stiffness data can provide closed-loop control of tissue maturation and monitoring or measuring of tissue maturity in a non-destructive manner. In-line sensing of cartilage stiffness may be correlated to tissue maturity by taking samples for cell assays, biochemical tests, imaging, and so forth. Based on the relationship between cartilage stiffness and tissue maturity, measurements of stiffness can be acquired and used as a surrogate for cartilage maturity, thus eliminating the need for destructive tests. Aspects of the present approach relate to the closed system culture of cartilage tissue in a uniaxial loading bioreactor equipped with real-time stiffness measurement capability.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A bioreactor system, comprising:
a sample support table configured to hold one or more flexible vessels each containing one or more tissue samples;
a force measurement sensor positioned so that when a respective flexible vessel is positioned on the sample support table at a measurement location, the respective flexible vessel rests on the force measurement sensor; and
an actuator configured to move along an axis to engage and disengage the respective flexible vessel when positioned at the measurement location such that, when engaged, the actuator generates a displacement and corresponding displacement data and the force measurement sensor measures the force and generates force data, wherein a tissue stiffness measure is calculated based on the displacement data and the force data,
wherein the bioreactor system further comprises a sample displacement means for rotating the sample support table, or linearly raising or lowering the sample support table or a component of the bioreactor system proximate the sample support table, along the axis of actuator motion.

2. A bioreactor system, comprising:
a sample support table configured to hold one or more flexible vessels containing tissue samples;
a first force measurement sensor positioned so that when a respective flexible vessel containing a tissue sample is positioned on the sample support table at a measurement location, the tissue sample is over the first force measurement sensor;
a second force measurement sensor disposed about the first force measurement sensor in a plane of or parallel to the sample support table, wherein the first force measurement sensor and second force measurement sensor can move independent of one another in a first direction perpendicular to the plane of the support table when in use; and
a linear actuator configured to move along an axis in the first direction and to come into contact with and displace the respective flexible vessel when the tissue sample of the respective flexible vessel is positioned over the first force measurement sensor.

3. The bioreactor system of claim 2, wherein the first force measurement sensor comprises a first force sensor having a cylindrical geometry and the second force measurement sensor comprises a second force sensor having a cylindrical ring geometry such that the first force sensor fits within the cylindrical ring defined by the second force sensor.

4. The bioreactor system of claim 2, wherein in a first measurement mode of the bioreactor system, the first force measurement sensor remains flush with the sample surface support table.

5. The bioreactor system of claim 4, wherein in the first measurement mode, the linear actuator in configured to compress the tissue sample against at least the first force measurement sensor to generate a compressive force measure.

6. The bioreactor system of claim 5, wherein in a second measurement mode of the bioreactor system, the first force measurement sensor is depressed with respect to a top surface of the sample surface support table and the second force measurement sensor to form a recess.

7. The bioreactor system of claim 6, wherein in the second measurement mode, the linear actuator in configured to compress the tissue sample to generate a shear force measure.

8. The bioreactor system of claim 7, wherein a Young's modulus and a Poisson's ratio of the tissue sample are calculated by using the shear force measure and the compressive force measure.

9. The bioreactor system of claim 2, wherein the first force measurement sensor and the second force measurement sensor measure a compressive force measure and a shear force measure, respectively, and wherein a Young's modulus and a Poisson's ratio of the tissue sample are calculated, based on the shear force measure and the compressive force measure, without directly contacting the tissue sample.

* * * * *